United States Patent [19]

Inoue et al.

[11] Patent Number: 5,770,627
[45] Date of Patent: Jun. 23, 1998

[54] HYDROPHOBICALLY-MODIFIED BIOADHESIVE POLYELECTROLYTES AND METHODS RELATING THERETO

[75] Inventors: Tadaaki Inoue, Osaka, Japan; Guohua Chen, Mountain View, Calif.; Allan S. Hoffman, Seattle, Wash.

[73] Assignees: University of Washington, Seattle, Wash.; Green Cross Corporation, Japan

[21] Appl. No.: 515,747

[22] Filed: Aug. 16, 1995

[51] Int. Cl.$^6$ .............................. A61K 47/32; A61K 9/10
[52] U.S. Cl. .................................... 514/772.1; 514/772.6; 424/487; 525/329.7
[58] Field of Search .............................. 424/78.08, 487; 514/772.6, 772.1; 525/329.7

[56] References Cited

U.S. PATENT DOCUMENTS

| Re. 34,902 | 4/1995 | Mitra et al. ........................... | 514/772.6 |
| 5,412,051 | 5/1995 | McCallum, III et al. ........... | 526/317.1 |
| 5,510,103 | 4/1996 | Yokoyama et al. ................... | 424/78.08 |

FOREIGN PATENT DOCUMENTS

| 126 684 A2 | 11/1984 | European Pat. Off. . |
| 629 649 A1 | 12/1994 | European Pat. Off. . |

OTHER PUBLICATIONS

Inoue et al., "Novel Hydrophobically–Modified Bioadhesive Polyelectrolytes for Controlled Drug Delivery to Mucosal Surfaces," in *Seventh International Symposium on Recent Advances in Drug Delivery Systems*, Feb. 27–Mar. 2, 1995, Salt Lake City, Utah, pp. 147–148.

Inoue et al., "A Novel Hydrophobically–Modified Polyelectrolyte Hydrogel for Drug Delivery," in *20th Annual Meeting of the Society for Biomaterials*, Apr. 5–9, 1994, Boston, MA, p. 154.

Chen and Hoffman, "Graft copolymers that exhibit temperature–induced phase transitions over a wide range of pH," *Nature* 373: 49–52, 1995.

Chen and Hoffman, "Thermal and pH–Sensitive Polymers For Use As Water Soluble–Insoluble Polymer–Enzyme Conjugates," in *19th Annual Meeting of the Society for Biomaterials*, Apr. 28–May 2, 1993, Birmingham, Alabama.

Chen and Hoffman, "Synthesis of Carboxylated Poly(NIPAAm) Oligomers and Its Application to Form Thermo–reversible Polymer–enzyme Conjugates," in *ACS Polymer Preprints*, Aug. 1992, pp. 468–469.

Hoffman, A., "Conventional and Environmentally–Sensitive Hydrogels for Medical and Industrial Uses: A Review Paper," in *Polymer Gels*, DeRossi et al. (eds.), Plenum Press, New York, 1991, pp. 289–297.

Chen et al., "Polymer–protein conjugates. I. Effect of protein conjugation on the cloud point of poly(N–isopropylacrylamide)," *Biomaterials* 11: 625–630, 1990.

Chen and Hoffman, "Polymer–protein conjugates. II. Affinity precipitation separation of human immunogammaglobulin by a poly(N–isopropylacrylamide)–protein A conjugate," *Biomaterials* 11: 631–634, 1990.

Dong and Hoffman, "Synthesis and Application of Thermally Reversible Heterogels for Drug Delivery," *Journal of Controlled Release* 13: 21–31, 1990.

Gombotz and Hoffman, "Immobilization of Biomolecules and Cells on and within Synthetic Polymeric Hydrogels," in *Hydrogels in Medicine and Pharmacy 1*, Chapter 5, 1986, pp. 95–126.

Okuyama et al., "Swelling controlled zero order and sigmoidal drug release from thermoresponsive poly(N–isopropylacrylamide–co–butyl methacrylate)hydrogel," *J. Biomater. Sci. Polymer Edn.* 4(5): 545–556, 1993.

Kim and Lee, "Hydrophobic Anionic Gel Beads for Swelling–Controlled Drug Delivery," *Pharmaceutical Research* 9(2): 195–199, 1992.

Yokoyama et al., "Preparation of Micelle–Forming Polymer–Drug Conjugates," *Bioconjugate Chem.* 3: 295–301, 1992.

Brannon–Peppas and Peppas, "Solute and Penetrant Diffusion in Swellable Polymers. IX. The Mechanisms of Drug Release from pH–Sensitive Swelling–Controlled Systems," *Journal of Controlled Release* 8:267–274, 1989.

Siegel et al., "pH–Controlled Release from Hydrophobic/Polyelectrolyte Copolymer Hydrogels," *Journal of Controlled Release* 8: 179–182, 1988.

Wang et al., "Viscometric behaviour of hydrophobically modified poly(sodium acrylate)," *Polymer Bulletin* 20: 577–582, 1988.

Park and Robinson, "Mechanism of Mucoadhesion of Poly(acrylic Acid) Hydrogels," *Pharmaceutical Research* 4(6): 457–464, 1987.

Peppas and Korsmeyer, "Dynamically Swelling Hydrogels in Controlled Release Applications," in *Hydrogels in Medicine and Pharmacy 3*, Chapter 6, 1987, pp. 109–135.

*Primary Examiner*—Peter F. Kulkosky
*Attorney, Agent, or Firm*—Seed and Berry LLP

[57] ABSTRACT

Hydrophobically-modified bioadhesive polyelectrolytes containing a bioadhesive polyelectrolyte and a hydrophobic component are disclosed. Also disclosed are polyelectrolyte-agent compositions wherein the hydrophobically-modified bioadhesive polyelectrolyte is loaded with a pharmaceutically, cosmetically, or prophylactically acceptable agent. Suitable agents have hydrophobic and/or ionic character, and include drugs. The polyelectrolyte-agent compositions may be formulated for administration by topical, oral and/or systemic routes. Methods of administering such agents to an animal are also disclosed, and include administration of an effective amount of the polyelectrolyte-agent composition to the animal.

25 Claims, 6 Drawing Sheets

HYDROPHOBICALLY-MODIFIED BIOADHESIVE POLYELECTROLYTES AND METHODS RELATING THERETO

TECHNICAL FIELD

This invention relates generally to polyelectrolytes and, more specifically, to hydrophobically-modified bioadhesive polyelectrolytes.

BACKGROUND OF THE INVENTION

Synthetic polymers are widely used as drug delivery vehicles due, at least in part, to their compositional diversity and good biocompatibility (Ottenbrite et al., *Polymers in Medicine Biomedical and Pharmaceutical Applications*, Technomic Publ. Co., Lancaster, Pa., 1992). Among them, water soluble polymers are of great interest as drug carriers due to their potential ability to release drug upon dissolution of the polymer. For example, erodible polymers which are capable of adhering to mucosal surfaces would be particular beneficial as a drug delivery vehicle.

While advances have been made in the field of erodible polymers, there is still a need in the art for novel and improved polymers, particularly in the area of sustained drug delivery. There is also a need for erodible polymers which are bioadhesive, as well as for methods related to the use thereof. The present invention fulfills these needs, and provides further related advantages.

SUMMARY OF THE INVENTION

In brief, the present invention is directed to a hydrophobically-modified bioadhesive polyelectrolyte. Accordingly, in one aspect of the present invention, a hydrophobically-modified bioadhesive polyelectrolyte is disclosed comprising a bioadhesive polyelectrolyte and a hydrophobic component. In a preferred embodiment, the bioadhesive polyelectrolyte is polyacrylic acid ("PAAc"), and the hydrophobic component is a hydrophobic polymer. In a particularly preferred embodiment, the hydrophobic polymer is oligo(methyl methacrylate) ("oMMA"). The hydrophobically-modified bioadhesive polyelectrolytes of the present invention include both block and graft copolymers of the bioadhesive polyelectrolyte and the hydrophobic component.

In another aspect of this invention, a polyelectrolyte-agent composition is disclosed comprising a hydrophobically-modified bioadhesive polyelectrolyte loaded with a suitable pharmaceutically, cosmetically and/or prophylactically acceptable agent. In one embodiment, the agent is a pharmaceutically acceptable drug.

In a further aspect of this invention, a method of administering a pharmaceutically, cosmetically and/or prophylactically acceptable agent to an animal in need thereof is disclosed. The method comprises administering to the animal an effective amount of a polyelectrolyte-agent composition comprising a hydrophobically-modified bioadhesive polyelectrolyte loaded with the pharmaceutically, cosmetically and/or prophylactically acceptable agent.

These and other aspects of the present invention will be apparent upon reference to the following detailed description and attached drawings.

DETAILED DESCRIPTION OF THE INVENTION

Figure 1:
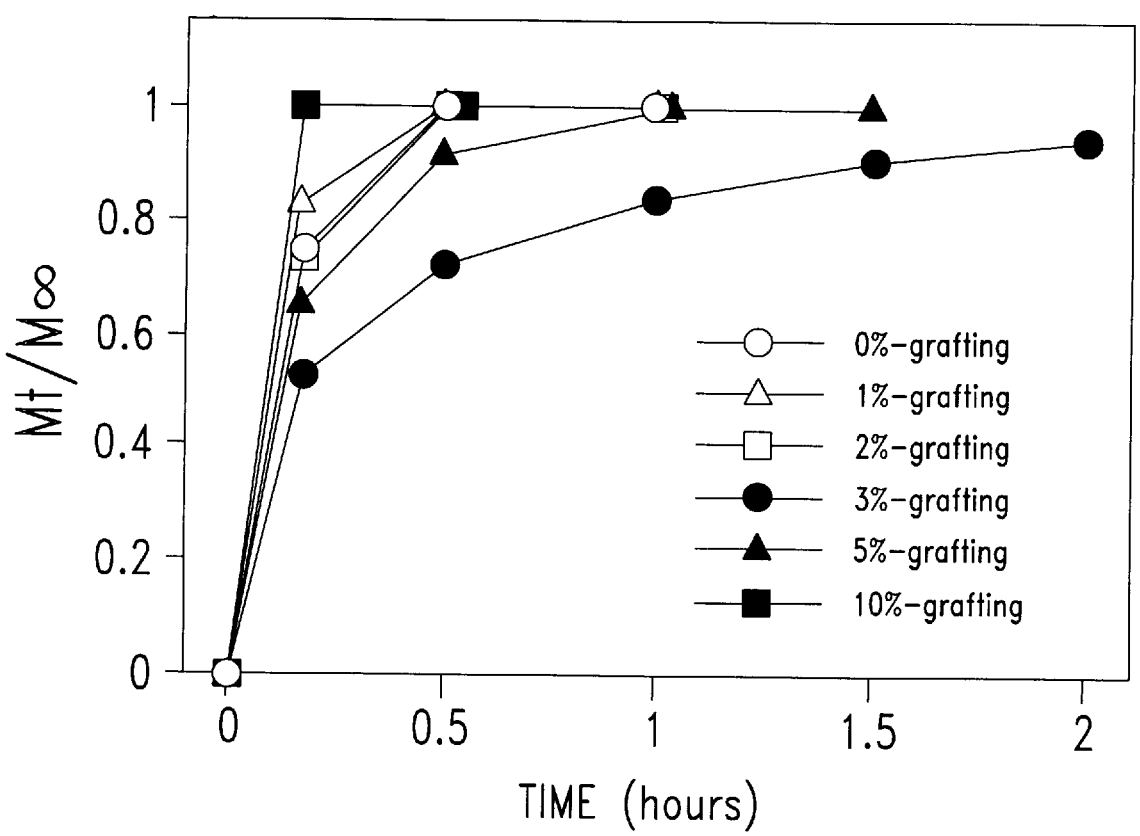
FIGS. 1, 2 and 3 illustrate the release of propranolol hydrochloride, theophylline and lysozyme, respectively, from PAAc and a graft copolymer of PAAc and MMA, oMMA-g-PAAc (MW oMMA: 11,000) in phosphate buffered saline (PBS) at room temperature.

As mentioned above, the present invention is generally directed to a hydrophobically-modified bioadhesive polyelectrolyte. More specifically, the polyelectrolyte of this invention is a bioadhesive polyelectrolyte having a hydrophobic component covalently attached thereto. In one embodiment, the hydrophobically-modified bioadhesive polyelectrolyte is a block copolymer and, in another embodiment, is a graft copolymer.

For purpose of clarity, a brief review of polymer nomenclature is helpful in understanding the present invention. In general, a polymer is a macromolecule (i.e., a long molecular chain) synthetically derived from the polymerization of monomer units or which exists naturally as a macromolecule (but which is still derived from the polymerization of monomer units). The links of the molecular chain are the monomer units. For example, polyacrylic acid (PAAc) is a polymer derived from the monomer acrylic acid (AAc). More specifically, PAAc is a "homopolymer," a polymer consisting of a single repeating unit, namely, AAc. In contrast, a "copolymer" is a polymer containing two (or more) different monomer units. A copolymer may generally be synthesized in several ways. For example, a copolymer may be prepared by the copolymerization of two (or more) different monomers. Such a process yields a copolymer where the two (or more) different monomers are randomly distributed throughout the polymer chain. These copolymers are known as "random copolymers." Alternatively, copolymers may be prepared by the covalent coupling or joining of two homopolymers. For example, the covalent coupling of one homopolymer to the terminus of a second, different homopolymer provides a "block copolymer". A block copolymer containing homopolymer A and homopolymer B may be schematically represented by the following formula:

where $(A)_x$ is a homopolymer of x monomers of A, $(B)_y$ is a homopolymer consisting of y monomers of B, and wherein the two homopolymers are joined by a suitable covalent bond or linking spacer group. While the above formula illustrates a block copolymer having two block components (i.e., a "di-blocked copolymer"), block copolymers may also have three (i.e., a "tri-blocked copolymer") or more block components.

Depending upon the chemical nature of the homopolymer components, an additional type of copolymer may also be prepared. For example, as mentioned above, PAAc is a homopolymer of AAc moieties. Consequently, the PAAc polymer chain is substituted with pendant carboxylic acid groups. The covalent coupling of a second, different homopolymer to one or more of these pendant carboxylic acid groups provides a "graft copolymer." Essentially, the second polymer is grafted onto the first. Thus, graft copolymers have a "backbone" polymer onto which one or more "pendant" polymers have been covalently attached. The nature of the graft copolymer may vary considerably depending upon the degree of substitution of the pendant polymers onto the backbone polymer. A graft copolymer having backbone homopolymer A onto which pendant homopolymer B is attached may be schematically represented by the following formula:

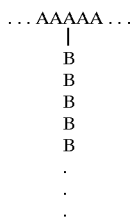

where "... AAAAA ..." is a homopolymer of monomer A, "BBBBB ..." is a homopolymer of B, and the two homopolymers are joined by a suitable covalent bond or linking spacer group.

While the block and graft copolymers discussed above contain homopolymers A and B, block and graft copolymers may also be formed from polymers other than homopolymers. For example, rather than grafting pendant homopolymer B to backbone homopolymer A, copolymer CD may be grafted to homopolymer backbone A to yield a graft copolymer where the pendant polymer is itself a copolymer. In this case, the copolymer CD may be either a block or random copolymer. Furthermore, homopolymer B or copolymer CD may be grafted to copolymer backbone EF (rather than homopolymer backbone A) to yield a graft copolymer where the backbone polymer is itself a block or random copolymer. Similarly, rather than joining homopolymer A to homopolymer B to obtain block copolymer AB, copolymer CD may be attached to homopolymer A to yield a block copolymer where one (or more) of the block components are copolymers.

Hydrophobically-modified bioadhesive polyelectrolytes of this invention include both block and graft copolymers. Both the block and graft copolymers of the present invention comprise a bioadhesive polyelectrolyte and a hydrophobic component. The block copolymers comprise a bioadhesive polyelectrolyte as one block, and at least one hydrophobic component as the other block. The graft copolymers of this invention comprise a bioadhesive polyelectrolyte as a backbone, and at least one pendant hydrophobic component grafted thereto. Alternatively, the hydrophobic component may serve as the backbone, with at least one bioadhesive polyelectrolyte grafted thereto. For both the block and graft copolymers of this invention, the bioadhesive polyelectrolyte may be a homopolymer, random copolymer or block copolymer. When the hydrophobic component of the block or graft copolymer is a hydrophobic polymer (as discussed in greater detail below), the hydrophobic polymer may be a homopolymer, random copolymer or block copolymer. Moreover, any combination thereof is within the scope of this invention.

The bioadhesive polyelectrolytes of this invention may generally be characterized as carboxylic acid-containing polymers. The carboxylic acid moieties of such polymers are typically capable of dissociating into two or more ions when contacted with, for instance, a biological fluid and/or mucosal tissue. This feature imparts bioadhesive properties to the polyelectrolyte via hydration and swelling upon contact with the biological fluid and/or mucosal tissue. For example the carboxylic acid groups of polyelectrolytes such as PAAc are ionized upon contact with biological fluids or mucosal tissues, and the uptake of cations (such as $Na^+$ and $K^+$) provides neutralized carboxylic acid moieties (e.g., $COO^-Na^+$). This ionization is accompanied by the uptake of water which, in turn, results in swelling and causes the polyelectrolyte to become "sticky" or bioadhesive.

Bioadhesive polyelectrolytes may be formed by polymerizing suitable monomers to yield a polymer by known techniques. More specifically, the polymer may be derived from polymerizable carboxylic acids, resulting in a synthetic carboxylic acid-containing polymer. Suitable synthetic carboxylic acid-containing polymers include polyacrylic acid (PAAc), polymethacrylic acid (PMAAc) and copolymers thereof. Alternatively, naturally-occurring carboxylic acid-containing polymers may be employed, such as hyaluronic acid.

As mentioned above, the hydrophobically-modified bioadhesive polyelectrolytes of the present invention also include a hydrophobic component. As used in the context of this invention, a hydrophobic component may be either a hydrophobic moiety or a hydrophobic polymer. A hydrophobic moiety includes a moiety derived from a hydrophobic compound including (but not limited to) cholesterol and phospholipids. Suitable phospholipids include phosphoglycerides derived from saturated and unsaturated C10–C24 fatty acids. The ratio of hydrophobic moiety to bioadhesive polyelectrolyte preferably ranges from 1 wt % to 50 wt %, and more preferably from 3 wt % to 30 wt %.

In the context of this invention, a hydrophobic polymer may be a homopolymer or a random or block copolymer, and is generally characterized as a polymer which is water insoluble and/or absorbs little or no water. In a preferred embodiment, the hydrophobic polymer absorbs less than 20 wt % water, and more preferably less than 10 wt % water. In one embodiment of this invention, the hydrophobic polymer is polymethyl methacrylate (PMMA).

Suitable hydrophobic polymers of this invention may contain monomers having the following general structures (I) through (VII).

where
n represents repeating monomer units of the hydrophobic polymer;
$R_1$ is selected from hydrogen and a saturated or unsaturated C1–C2 alkyl; and
$R_2$ is selected from hydrogen, a saturated or unsaturated C1–$C_2$ alkyl, a substituted or unsubstituted C6–C9 aryl, a substituted or unsubstituted C7–C11 arylalkyl, —C(=O)N($R_3$)($R_4$) and —C(=O)O$R_5$, where $R_3$ and $R_4$ are the same or different and independently selected from a saturated or unsaturated C1–C3 alkyl, and $R_5$ is selected from a saturated or unsaturated C1–C2 alkyl and —(CH$_2$)$_m$OH where m is $\geq$3;

where
n represents repeating monomer units of the hydrophobic polymer; and
$R_6$ and $R_7$ are the same or different and independently selected from hydrogen, a C1–C6 alkoxy (i.e., —O-alkyl), a saturated or unsaturated C1–C6 alkyl, a substituted or unsubstituted C6–C9 aryl, and a substituted or unsubstituted C7–C11 arylalkyl;

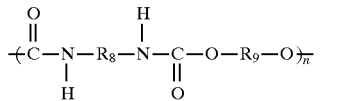

where n represents repeating monomer units of the hydrophobic polymer; and $R_8$ and $R_9$ are the same or different and independently selected from —$(CH_2)_m$— where m=2–6, a substituted or unsubstituted C6–C9 aryl, a substituted or unsubstituted C7–C11 arylalkyl, a substituted or unsubstituted C12–C18 diphenyl, and a substituted or unsubstituted C13–C22 diphenylalkyl (such as methylene diphenyl);

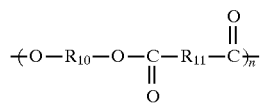

where n represents repeating monomer units of the hydrophobic polymer; and $R_{10}$ and $R_{11}$ are the same or different and independently selected from a saturated or unsaturated C1–C6 alkyl, a substituted or unsubstituted C6–C9 aryl, and a substituted or unsubstituted C7–C11 arylalkyl;

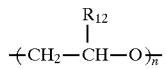

where n represents repeating monomer units of the hydrophobic polymer; and $R_{12}$ is selected from a saturated or unsaturated C1–C3 alkyl;

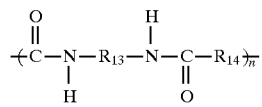

where n represents repeating monomer units of the hydrophobic polymer; and $R_{13}$ and $R_{14}$ are the same or different and independently selected from —$(CH_2)_m$— where m=4–10, a substituted or unsubstituted C6–C9 aryl, a substituted or unsubstituted C7–C11 arylalkyl, a substituted or unsubstituted C12–C18 diphenyl, and a substituted or unsubstituted C13–C22 diphenylalkyl; and

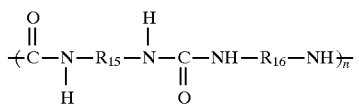

where n represents repeating monomer units of the hydrophobic polymer; and $R_{15}$ and $R_{16}$ are the same or different and independently selected from —$(CH_2)_m$— where m=4–10, a substituted or unsubstituted C6–C9 aryl, a substituted or unsubstituted C7–C11 arylalkyl, a substituted or unsubstituted C12–C18 diphenyl, and a substituted or unsubstituted C13–C22 diphenylalkyl.

In a preferred embodiment of structures (I) through (VII) above, the saturated or unsaturated alkyl is a saturated n-alkyl. Preferred substituted or unsubstituted C6–C9 aryl moieties include phenyl (—$C_6H_5$), methylphenyl (—$C_6H_4$($CH_3$)), dimethylphenyl (—$C_6H_3(CH_3)_2$) and trimethylphenyl (—$C_6H_2(CH_3)_3$), and preferred C7–C11 arylalkyl moieties include benzyl (—$CH_2C_6H_5$), methylbenzyl (—$CH_2C_6H_4(CH_3)$), dimethylbenzyl (—$CH_2C_6H_3(CH_3)_2$), phenylethyl (—$CH_2CH_2C_6H_5$) and phenylpropyl (—$CH_2CH_2CH_2C_6H_5$).

While the various R moieties of structures (I) through (VII) above contain hydrogen or hydrogen-substituted carbon atoms, one or more of the hydrogen atoms can be replaced with a halogen or halogens, particularly fluorine. For example, when an R moiety is —$CH_3$, a corresponding fluorine-substituted R moiety is, for example, —$CF_3$. Similar fluorine substitutions may be made to each hydrogen atom identified above in structures (I) through (VII).

The hydrophobic polymers of this invention also include all combinations of structures (I) through (VII)—that is, the hydrophobic polymer may be a homopolymer of any one of structures (I) through (VII), or may be a random or block copolymer (or any combination thereof) of two (or more) monomers represented by structures (I) through (VII). Suitable hydrophobic polymers may also include other hydrophobic monomer units, and/or non-hydrophobic monomer components, including one or more hydrophilic monomers. Suitable hydrophilic monomers include (but are not limited to) 2-hydroxy ethyl methacrylate (HEMA), vinyl pyrrolidone, vinyl acetate (hydrolysed to the alcohol) and acrylamide. In this context, the hydrophilic monomer must not be present at a level such that the hydrophobic polymer losses its hydrophobicity (i.e., the hydrophobic polymer must remain water insoluble). In general, hydrophobic monomers comprise in excess of 80 mole percent of the hydrophobic polymer, while the precise mole percent will depend upon the hydrophilicity of any hydrophilic monomer units present in the hydrophobic polymer.

The hydrophobic polymer of the hydrophobically-modified bioadhesive polyelectrolytes of the present invention preferably have average molecular weights in the range from 500 to 30,000, preferably from 1,000 to 15,000, and more preferably from 3,000 to 10,000. In addition, the ratio of hydrophobic polymer to bioadhesive polyelectrolyte preferably ranges from 1 wt % to 50 wt %, and more preferably from 3 wt % to 30 wt %.

With regard to synthesis of the hydrophobically-modified bioadhesive polyelectrolytes of this invention, such polyelectrolytes may generally be synthesized by covalent coupling of a hydrophobic component to a bioadhesive polyelectrolyte. The covalent link between the two components should be resistant to cleavage, and suitable covalent linkages include (but are not limited to) amide, ester, ether, thioester, thioether, urea, urethane and amine linkages. Such linkages result from the coupling of a suitably reactive hydrophobic component with a complementary and suitably reactive bioadhesive polyelectrolyte. For example, an amide linkage may be prepared by coupling an amino-terminated hydrophobic component with a carboxylic acid group of the bioadhesive polyelectrolyte. Other suitable linkages may be prepared by standard techniques.

Hydrophobically-modified bioadhesive polyelectrolytes may be prepared by the coupling of two homopolymers (e.g., a polyelectrolyte homopolymer and a hydrophobic homopolymer), a homopolymer and a copolymer (e.g., a polyelectrolyte homopolymer and a hydrophobic copolymer or a polyelectrolyte copolymer and a hydrophobic homopolymer), or two copolymers (e.g., a polyelectrolyte copolymer and a hydrophobic copolymer). Furthermore, two (or more) different hydrophobic homopolymers or copolymers can be joined to a single polyelectrolyte, and/or the polyelectrolyte can contain two (or more) different homopolymers or copolymers.

For the hydrophobically modified bioadhesive polyelectrolytes of the present invention having a hydrophobic component that is a hydrophobic moiety rather than a hydrophobic polymer, the hydrophobic moiety may be covalently linked to the terminus of the bioadhesive polyelectrolyte to provide a block copolymer. Similarly, the hydrophobic moiety may be coupled as a pendant group to a bioadhesive polyelectrolyte backbone to provide a graft copolymer.

In one embodiment, the hydrophobically-modified bioadhesive polyelectrolytes of the present invention have a bioadhesive polyelectrolyte backbone with one or more pendant hydrophobic components attached thereto. The degree of substitution of the pendant hydrophobic component on the bioadhesive polyelectrolyte backbone may be controlled by the chemical coupling reaction. For example, by adjusting the ratio of pendant groups to be reacted with the polyelectrolyte backbone, the properties of the resulting hydrophobically-modified bioadhesive polyelectrolyte may be controlled and optimized. Accordingly, a balance in the bioadhesive polyelectrolyte ratio to the hydrophobic component grafted thereto provides an optimum polymer which exhibits preferred properties for any given application. A balance in the bioadhesive polyelectrolyte ratio to the hydrophobic component for the block copolymers of this invention can be similarly optimized.

Hydrophobically-modified bioadhesive polyelectrolytes have wide industrial application, and are particularly useful for the sustained and/or controlled release of pharmaceutically, cosmetically and/or prophylactically acceptable agents. Such agents may have ionic, polar and/or hydrophobic character. Furthermore, agents of this invention can be modified by known techniques to render them more or less ionic, polar and/or hydrophobic. As used herein, hydrophobic agents are only sparingly soluble in water, and generally have solubilities less than 100 ppm. In one embodiment, the agent may be hydrophobic (such as β-estradiol) or in another embodiment, may have a hydrophobic portion and an ionic portion (such as propranolol, doxorubicin and indomethacin). In a further embodiment, the agent may have multiple cationic charges (such as lysozyme). Representative examples of an agent lacking a hydrophobic portion and having only a single charge are theophylline and caffeine, and are generally not suitable for optimal, sustained delivery by the hydrophobically-modified bioadhesive polyelectrolytes of this invention.

Based on the disclosure herein, one skilled in the art could readily determine whether any given agent is suitable for sustained and/or controlled release by the hydrophobically-modified bioadhesive polyelectrolyte of this invention. In one embodiment of this invention, the agent released by the hydrophobically-modified bioadhesive polyelectrolyte is a drug, including compounds, peptides and proteins. As used in the context of this invention, the term "drug" includes the definition set forth in 21 C.F.R. §201(g)(1), "Federal Food, Drug, and Cosmetic Act Requirements relating to Drugs for Human and Animal Use" (hereby incorporated by reference). Under this definition, a drug means (a) articles recognized in the official United States Pharmacopeia, official Homeopathic Pharmacopeia of the United States, or official National Formulary, or any supplement thereof; and (b) articles intended for use in the diagnosis, cure, mitigation, treatment, or prevention of disease in man or other animals; and (c) articles (other than food) intended to affect the structure of any function of the body of man or other animals; and (d) articles intended for use as a component of any articles specified in clause (a), (b) or (c) above; but does not include devices or their components, parts or accessories.

In another embodiment, agents having activity relating to skin care, hair care (including hair follicles), care of nails, and toiletries, perfumes and fragrances are also included within the scope of this invention. In addition, the agent may also be selected from fertilizers, pesticides, fungicides and herbicides.

The hydrophobically-modified bioadhesive polyelectrolytes of this invention are particularly useful for the sustained and controlled release of hydrophobic and/or ionic agents as defined above. The combination of a hydrophobically-modified bioadhesive polyelectrolyte of this invention with one or more agents is referred to herein as a polyelectrolyte-agent composition. Such compositions may take a variety of forms, including (but not limited to) particles, films, solutions, suspensions and micelles. For example in the case of solutions, the hydrophobically-modified bioadhesive polyelectrolyte may be equilibrated in a solution containing one or more agents. Such solutions may then be dried to yield polyelectrolyte-agent compositions in the form of particles and/or films. In the case of particles, such particles may generally have a diameter of less than 1 mm, and are more typically about 0.5 mm in diameter. Depending upon its intended use, the particles may be further reduced in size by mechanical milling or grinding techniques.

In one embodiment, the hydrophobically-modified bioadhesive polyelectrolytes of the present invention provide effective delivery and sustained release of hydrophobic agents. Through the presence of their hydrophobic components and the formation of micelles or "polysoaps," the hydrophobically-modified bioadhesive polyelectrolytes of this invention effectively solubilize and permit the delivery of hydrophobic agents. Such solubilization and delivery is due to the hydrophobic nature of the interior of the micelle or polysoap which provides an environment suitable for the solubilization and transport of a hydrophobic agent. In contrast, the hydrophilic exterior of the micelle or polysoap facilitates its aqueous solubility.

While a hydrophobic agent is generally carried within the hydrophobic region of the micelle or polysoap, in another embodiment such micelles or polysoaps may also effectively transport and provide sustained release of a polycationic agent. Such transport and sustained release is effected through the ionic interaction of the polycationic agent with the negatively charged exterior of the micelle or polysoap. In effect, the polycationic agent serves to link one micelle or polysoap with another. In such a complex, the ionic interaction between the micelle or polysoap and the polycationic agent provides for the sustained release. Upon swelling of the bioadhesive polyelectrolyte, the strength of the interaction between the polyelectrolyte and polycationic agent is lessened, thus ultimately permitting the release of the agent. In the practice of the present invention, representative polycationic agents include polycationic proteins such as lysozyme and growth factors.

The polyelectrolyte-agent compositions of this invention may be administered in any suitable manner, including (but not limited to) topical and systemic routes of administration.

Topical administration includes application to the skin, eye, nose, mouth, throat, scalp, an open wound or burn, and mucosal tissue in general (such as the respiratory and alimentary tracts, rectum and vagina), and which contains sufficient water/ion content to hydrate the polyelectrolyte-agent composition. Systemic administration includes all forms of injection, as well as systemic administration by oral administration.

The polyelectrolyte-agent compositions may be formulated using known formulation techniques in any manner suitable for its end application. For example, the polyelectrolyte-agent composition may be suspended or emulsified within a solution containing an acceptable carrier or diluent, or combined with, for example, a solution, cream, gel, ointment or powder. Solutions, creams, gels, ointments and powders are, for example, preferred for topical applications. Typically, suitable agent concentrations in the bioadhesive polyelectrolyte polymer of these formulations range from 0.1% to 50% by weight, and preferably from 0.5% to 30% by weight. Polyelectrolyte-agent compositions may also be formulated as a tablet, capsule or suppository. To this end, suppository formulations may be particularly suited for rectal administration of the polyelectrolyte-agent compositions, while tablet and capsule forms are suitable for oral administration. The polyelectrolyte-agent composition may also be formulated for nasal or buccal administration by known techniques. Formulations for general systemic delivery are also readily prepared using known techniques. Furthermore, the polyelectrolyte-agent compositions may be implanted in an animal by, for example, subcutaneous or intramuscular implantation, or may be implanted into bone.

In addition to use as vehicles for the sustained and controlled release of agents, the hydrophobically-modified bioadhesive polyelectrolytes of this invention have utility for a variety of other applications, including (but not limited to) uses relating to separation techniques, diagnostics, and bioreactions with immobilized ligands or reactants.

The following examples are provided for purposes of illustration, not limitation.

EXAMPLES

Source of Materials

Methyl methacrylate (MMA), acrylic acid (AAc), and N,N-dimethylformamide (DMF), ACS reagent were purchased from Aldrich Chemical Company, Inc., Milwaukee, Wis. and were used after distillation under reduced pressure. 2,2'-azobisbutyronitrile (AIBN) and 2-amino ethanethiol hydrochloride (AET) were purchased from Aldrich Chemical Company, Inc. and were used after recrystallization with methanol. The following materials were purchased from the identified manufacturer and used as received: ethyleneglycol dimethacrylate (EGDMA), dicyclohexyl carbodiimide (DCC), and ammonium persulfate (APS) were purchased from Aldrich Chemical Company, Inc.; tetrahydrofuran, HPLC grade was purchased from Aldrich Chemical Company, Inc.; polyacrylic acid (MW: 200,000); diethyl-ether; poly (methyl methacrylate) standards were purchased from American Polymer Standards Corporation (Mentor, Ohio); theophylline was purchased from Fluka Chemika-BioChemika (Ronkonkoma, N.Y.); propranolol hydrochloride was purchased from Aldrich Chemical Company; lysozyme (from chicken egg white, L-6876) and doxorubicin hydrochloride were purchased from Sigma Chemical Company (St. Louis, Mo.); and absolute ethanol was purchased from Midwest Grain Co. (Perkin, Ill.). All other chemicals were of reagent grade.

EXAMPLE 1

Preparation of Amino-Terminated Hydrophobic Polymers: Amino-Terminated oMMA and Amino-Terminated o(HEMA-co-MMA)

In this example, the preparation of two representative hydrophobic polymers are described. In particular, this example discloses the preparation of (a) a hydrophobic homopolymer, amino-terminated oligo(methyl methacrylate) ("oMMA"), and (b) a hydrophobic random copolymer, amino-terminated co-oligo(hydroxy ethyl methacrylate-co-methyl methacrylate) ("o(HEMA-co-MMA)").

A. Amino-terminated oMMA

Amino-terminated oMMA was prepared by free radical polymerization of MMA using AIBN as an initiator and AET as a chain transfer agent. The reaction was performed in a sealed ampule at 60° C. in DMF solution. Before the reaction, the reaction mixture was subjected to repeated freeze thaw cycles using liquid nitrogen as a coolant. When the reaction mixture was frozen, the ampule was degassed using a vacuum pump. Finally, the reaction was carried out under vacuum. After the reaction, the oMMA was precipitated by water. The precipitate was filtered and washed with water, then dried in vacuum. Three amino-terminated oMMA with different molecular weights were prepared by changing the ratio of the chain transfer agent to the monomer from 2 to 8 mol %.

The molecular weight of each amino-terminated oMMA was determined by gel permeation chromatography (GPC) using poly(methyl methacrylate) as standards. GPC was carried out using a Waters 501 HPLC (Millipore Corporation, Milford, Mass.) connected in series with Waters Ultrastyragel $10^4$ Å, $10^3$ Å and 500 Å columns. Tetrahydrofuran was utilized as the eluent at a flow rate of 0.7 ml/min. at room temperature. The polymers were detected by refraction index with a Waters 410 Differential Refractometer. It was found that, as the ratio of the chain transfer reagent increased, the molecular weight of the amino-terminated oMMA decreased. The results of this experiment are presented in Table 1.

TABLE 1

| Molecular Weights of Amino-Terminated oMMA | | | | |
|---|---|---|---|---|
| MMA:AIBN:AET (mole ratios) | Polymerization (time, hr.) | Yield (w/w %) | $M_n$ | $(M_w/M_n)$ |
| 100:0.5:2 | 4 | 55 | 11,000 | 2.4 |
| 100:0.5:4 | 6 | 78 | 6,600 | 2.0 |
| 100:0.5:8 | 14 | 56 | 4,700 | 1.8 |

B. Amino-terminated o(HEMA-co-MMA)

Amino-terminated random co-oligomer of hydroxy ethyl methacrylate (HEMA) and methyl methacrylate (MMA), o(HEMA-co-MMA), was prepared by free radical copolymerization of HEMA and MMA using AIBN as an initiator and AET as a chain transfer agent. The copolymerization was carried out as described above for the amino-terminated oMMA, and yielded a co-oligomer comprising 10 mol % HEMA and 90 mol % MMA.

EXAMPLE 2

Preparation of Hydrophobically-Modified Bioadhesive Polyelectrolytes: oMMA-g-PAAc and o(HEMA-co-MMA)-g-PAAc In this example, the preparation of two representative, hydrophobically-modified bioadhesive polyelectrolytes are described. Specifically, this example discloses the preparation of two graft copolymers: (a) oMMA-g-PAAc having a pendant hydrophobic homopolymer component, oMMA, and a PAAc backbone, and (b) o(HEMA-co-MMA)-g-PAAc having a pendant hydrophobic random copolymer component, o(HEMA-co-MMA), and a PAAc backbone.

A. oMMA-g-PAAc

The oMMA-g-PAAc polyelectrolyte was prepared by coupling the amino-terminated oMMA of Example 1 onto a backbone of PAAc through reaction of the terminal oMMA amino group with an activated carboxyl group on PAAc using DCC as an activation reagent. This reaction is illustrated below:

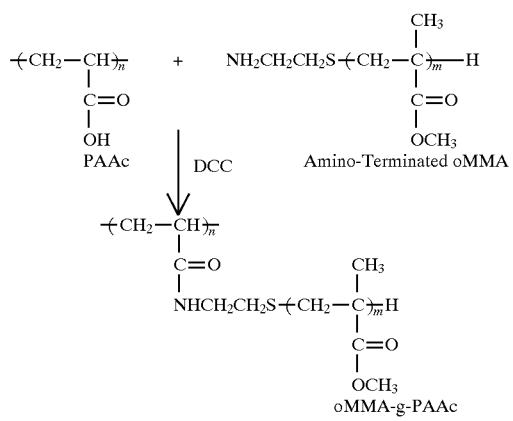

Specifically, PAAc was placed into a screw-capped glass vial, and a DMF solution of amino-terminated oMMA was then added and dissolved. After adding DCC, the solution was reacted for 24 hours at room temperature. After the reaction, the resulting oMMA-g-PAAc was precipitated by diethylether. The precipitate was filtered and washed with diethylether. The oMMA-g-PAAc was then air-dried for three days, and then completely dried in vacuum at 40° C. In this example, oMMA-g-PAAc was prepared having an oMMA grafting level which varied from 1 to 20 w/w %.

B. o(HEMA-co-MMA-g-PAAc

The o(HEMA-co-MMA)-g-PAAc polyelectrolyte was similarly prepared by coupling the amino-terminated oHEMA-co-MMA of Example 1 onto the backbone of PAAc through the reaction of the terminal amino group with an activated carboxyl group of PAAc using DCC as an activation agent as described above for the preparation of oMMA-g-PAAc. In this experiment, o(HEMA-co-MMA)-g-PAAc was prepared having an oHEMA-co-MMA grafting level which varied from 5 to 30 w/w %.

EXAMPLE 3

Solubility of Hydrophobically-Modified Bioadhesive Polyelectrolytes: oMMA-g-PAAc and o(HEMA-co-MMA)-g-PAAc The solubility properties of the representative hydrophobically-modified bioadhesive polyelectrolytes prepared by the procedures of Example 2 were evaluated, and are summarized in Table 2 (where "+" is soluble and "−" is insoluble).

TABLE 2

Solubility of Representative Hydrophobically-Modified Bioadhesive Polyelectrolytes in PBS

| Hydrophobically-Modified Bioadhesive Polyelectrolytes | Grafting Level (w/w %) | | | | | |
|---|---|---|---|---|---|---|
|  | 1 | 2 | 3 | 5 | 10 | 20 |
| oMMA-g-PAAc (MW of oMMA: 4200) | + | − | − | − | − | − |
| oMMA-g-PAAc (MW of oMMA: 11000) | + | + | − | − | − | − |

TABLE 2-continued

Solubility of Representative Hydrophobically-Modified Bioadhesive Polyelectrolytes in PBS

| Hydrophobically-Modified Bioadhesive Polyelectrolytes | Grafting Level (w/w %) | | | | | |
|---|---|---|---|---|---|---|
|  | 1 | 2 | 3 | 5 | 10 | 20 |
| o(HEMA-co-MMA)-g-PAAc (10 mol % HEMA) | + | + | + | + | + | − |
| o(HEMA-co-MMA)-g-PAAc (20 mol % HEMA) | + | + | + | + | + | − |

Referring to Table 2, the solubility of the graft, hydrophobically-modified bioadhesive polyelectrolytes in PBS depended on the grafting level of the hydrophobic polymer onto the bioadhesive polyelectrolyte backbone. In addition, solubility increased with an increase in chain length of the hydrophobic polymer. Furthermore, the solubility of o(HEMA-co-MMA)-g-PAAc was found to be greater than the corresponding oMMA-g-PAAc.

EXAMPLE 4

Agent Loading of Hydrophobically-Modified Bioadhesive Polyelectrolytes to Yield Polyelectrolyte-Agent Compositions In this example, the hydrophobically-modified bioadhesive polyelectrolytes prepared in Example 2 were loaded with an agent to yield polyelectrolyte-agent compositions of this invention.

Specifically, PAAc, oMMA-g-PAAc and o(HEMA-co-MMA)-g-PAAc polyelectrolytes were individually loaded with an agent selected from theophylline, propranolol hydrochloride or lysozyme. Propranolol hydrochloride is a representative agent having both a hydrophobic portion and an ionic portion, while lysozyme is a representative polycationic agent (lysozyme is a protein of 129 amino acids having 18 basic amino acids and with a pI of 11, and at neutral pH it is highly positively charged.) Theophyllilne is an agent possessing only a single charge, and is not a preferred agent within the context of this invention.

The dried oMMA-g-PAAc and o(HEMA-co-MMA)-g-PAAc of Example 2 were dissolved in separate vials containing an 80/20 (v/v) ethanol/water solution in combination with 0.1 w/v % of theophylline or propranolol hydrochloride. The solution was placed on the bottom of a 20 ml screw-capped glass vial, air dried at room temperature, and then completely dried in vacuum. In the case of lysozyme loading, dried oMMA-g-PAAc and o(HEMA-co-MMA)-g-PAAc was dissolved in 80/20 (v/v) ethanol/water. This solution was then placed on the bottom of a 20 ml screw-capped glass vial, air dried at room temperature, and completely dried in vacuum. Lysozyme dissolved in 50 nM phosphate buffer (0.1 w/v %, pH 7.4), was added onto the dried polyelectrolyte and equilibrated. The lysozyme-loaded polyelectrolyte was then air dried at room temperature, and completely dried in vacuum.

EXAMPLE 5

Agent Release from Polyelectrolyte-Agent Compositions

In this example, release of representative agents from the polyelectrolyte-agent compositions of Example 4 is disclosed.

Polyelectrolyte-agent compositions, in the form of thin films, were prepared according to Example 4. Ten (10) ml of PBS buffer was added to each of the 20 ml screw-capped glass vials containing the polyelectrolyte-agent composition, and shaken by an Orbit shaker (model 3540, Lab-line Instruments, Inc., Melrose Park, Ill.) at a shaking speed of 300 rpm and at room temperature. Next, 0.5 ml of the PBS solution was withdrawn from the vials periodically, and the amount of released agent contained within the PBS solution was determined spectrophotometrically. The volume of the PBS in the vials was held constant by adding 0.5 ml of fresh PBS buffer after each sampling. The fractional release of agent from the polyelectrolyte-agent compositions was calculated as a function of time, with all data averaged over three determinations. Release of agent from agent-loaded PAAc (i.e., 0% graft) was determined for comparison purpose.

Referring to FIG. 1, release of propranolal hydrochloride from PAAc (0% graft) and oMMA-g-PAAc at grafting levels of 1, 2, 3, 5 and 10 w/w % is depicted. Release of propranolol hydrochloride from oMMA-g-PAAc initially slowed with an increase in the oMMA grafting level (up to about 3%), but at higher grafting levels (such as 5% and 10%), where the copolymer no longer dissolves in PBS, the agent released more rapidly. The existence of a macroporous structure is suggested by these data for such higher graft level, insoluble copolymers.

Figure 2:
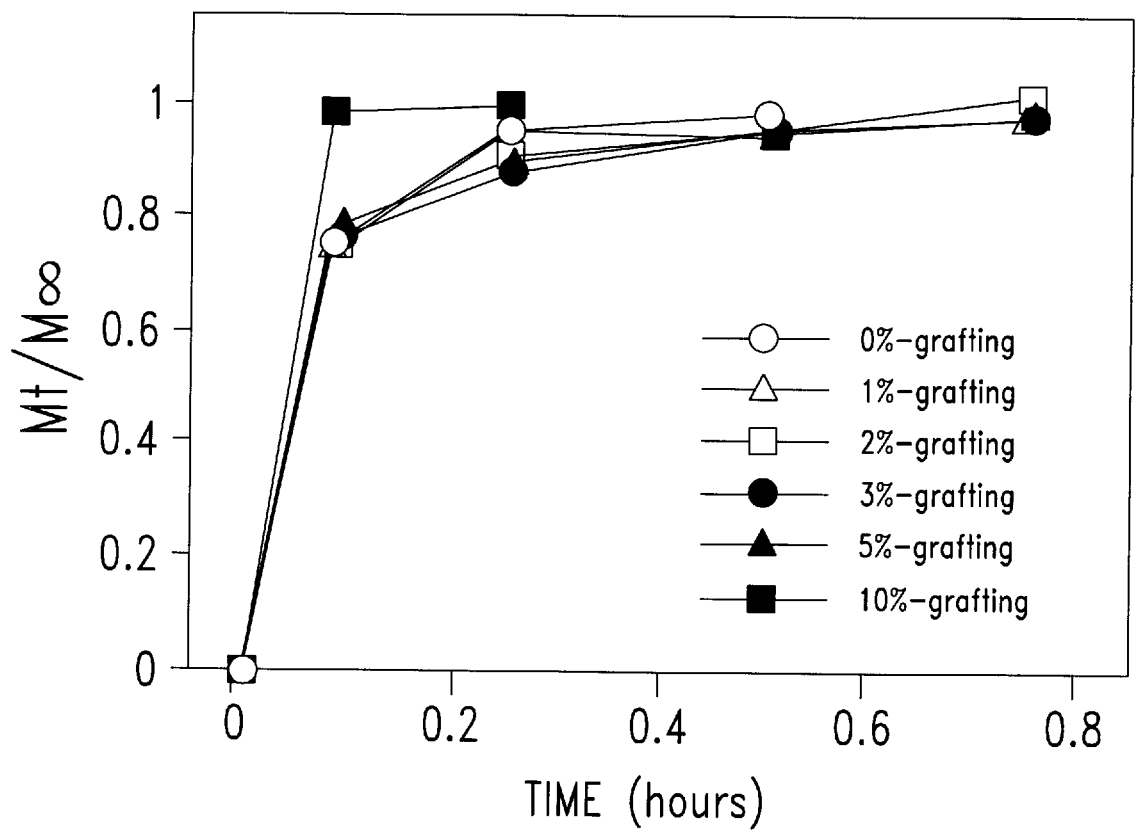

FIG. 2 illustrates release of a less preferred agent, theophylline, from PAAc (0% graft) and oMMA-g-PAAc at grafting levels of 1, 2, 3, 5 and 10 w/w %. Theophylline possesses only a single charge and was observed to release relatively rapidly from the polyelectrolyte-agent composition of this example.

Figure 3:
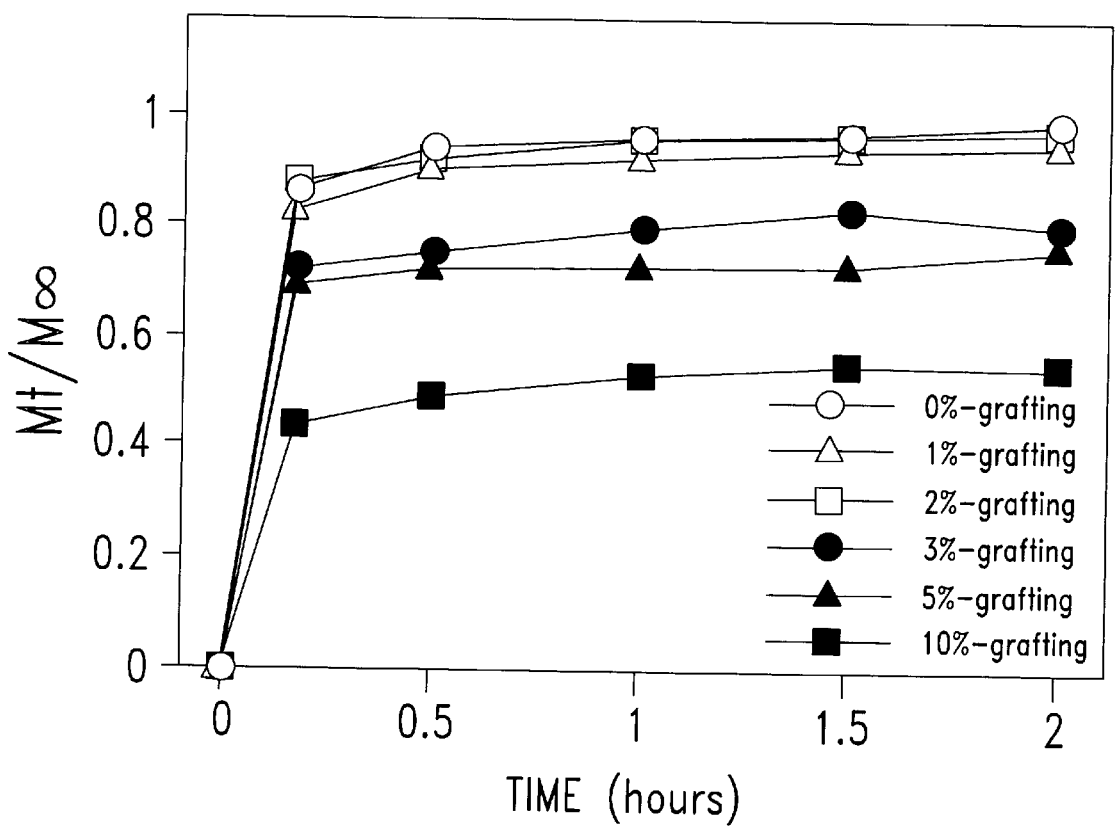

FIG. 3 illustrates release of a polycationic agent, lysozyme, from PAAc (0% graft) and oMMA-g-PAAc at grafting levels of 1, 2, 3, 5 and 10 w/w %. Release of lysozyme from oMMA-g-PAAc was affected by the grafting level. At higher grafting levels (such as 10%), lysozyme was retained in the copolymer (i.e., only about 50% of the lysozyme was released after 2 hours, and the amount of retained lysozyme was proportional to the grafting level.

Figure 4:
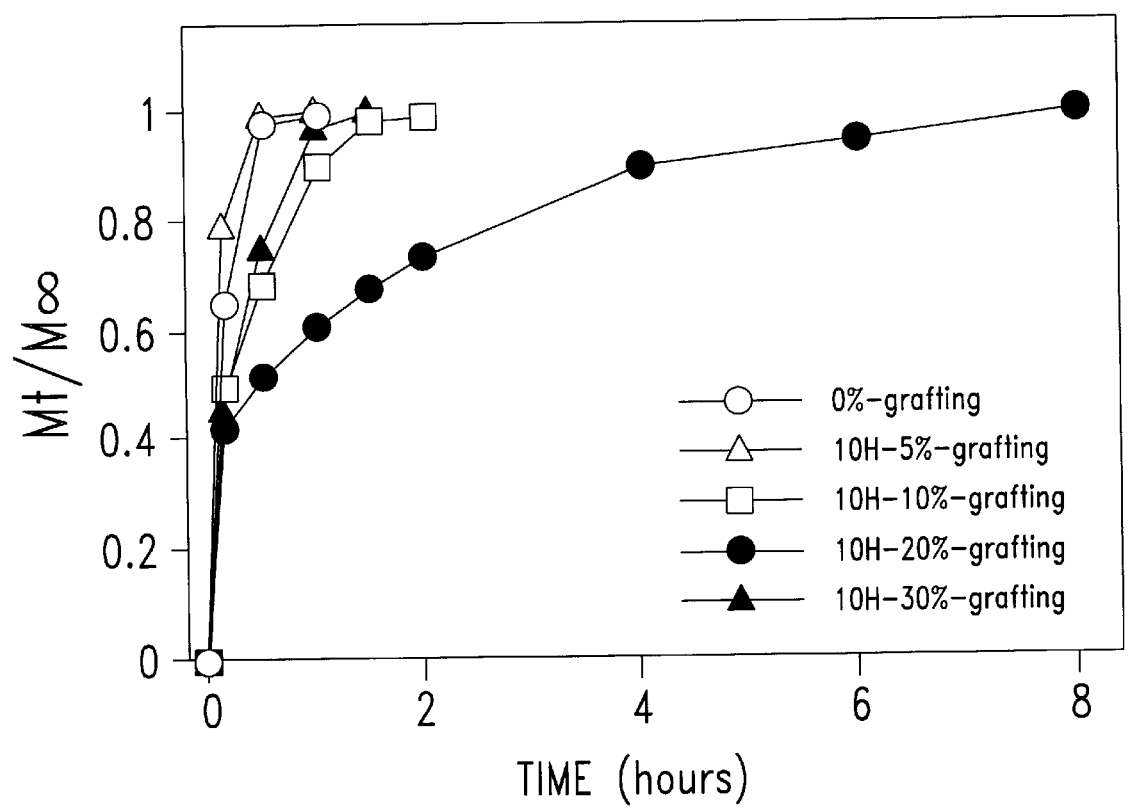
FIGS. 4 and 5 illustrate the release of propranolol hydrochloride and lysozyme, respectively, from PAAc and a graft copolymer of PAAc and HEMA-co-MMA, o(HEMA-co-MMA)-g-PAAc (co-oligomer: 10 mol % HEMA, 90 mol % MMA) in PBS at room temperature.

FIG. 4 depicts release of propranolol hydrochloride from PAAc (0% graft) and o(HEMA-co-MMA)-g-PAAc at grafting levels at 5, 10, 20 and 30 w/w %. Increase agent release time was observed (relative to the data of FIG. 1) by the introduction of HEMA into the hydrophobic polymer at an optimal grafting level of 20 w/w %.

Figure 5:
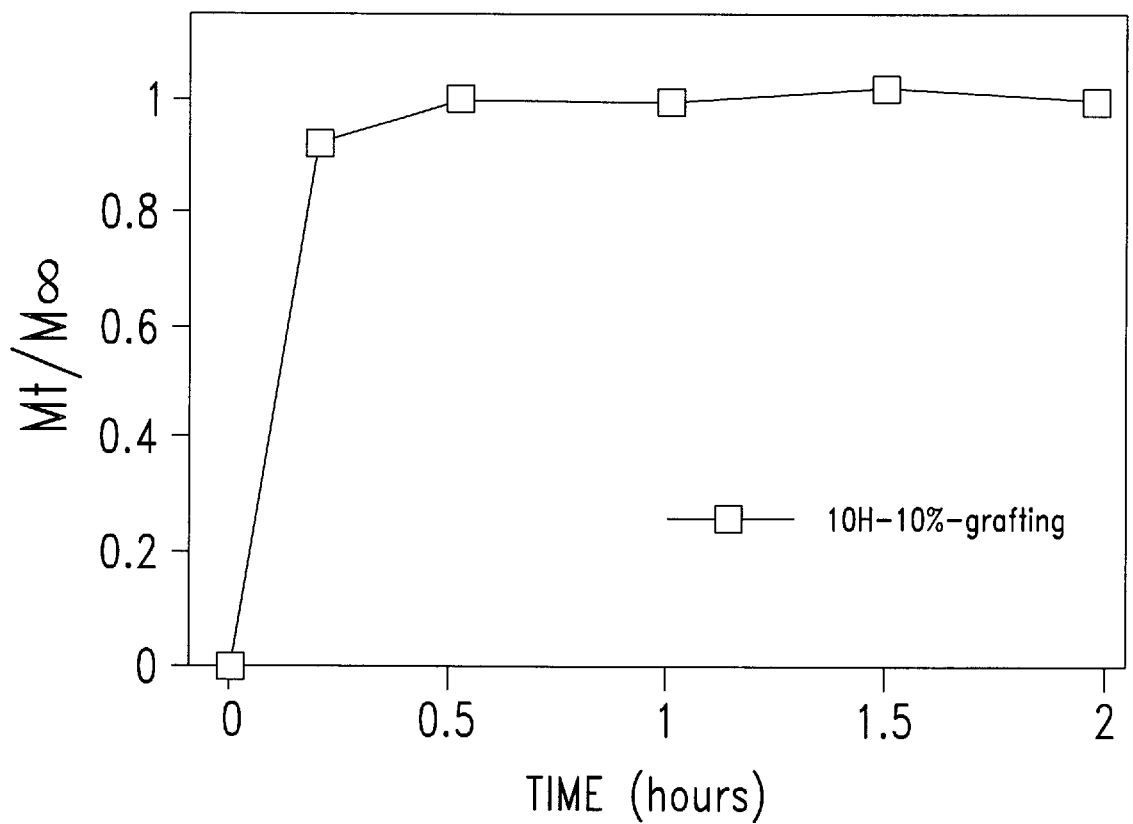

Release of lysozyme from o(HEMA-co-MMA)-g-PAAc at a grafting level of 10 w/w % is presented in FIG. 5. In contrast to the release of lysozyme from oMMA-g-PAAc illustrated in FIG. 3, lysozyme release from o(HEMA-co-MMA)-g-PAAc was complete (i.e., 100% release). Thus, by varying the amount of HEMA introduced into the hydrophobic polymer, the release rate of lysozyme from the polyelectrolyte-agent composition can be controlled and optimized.

EXAMPLE 6

Preparation of Hydrophobically-Modified Bioadhesive Polyelectrolyte: oMMA-b-PAAc In this example, the preparation of a block, hydrophobically-modified bioadhesive polyelectrolyte, oMMA-b-PAAc, is disclosed.

Amino-terminated oMMA was prepared according to Example 1 and reacted with dithiobis(succinimidyl propionate), resulting in a dimer of the amino-terminated oMMA through a disulfide bond. The dimer was then reduced by dithiothreitol for 18 hours, yielding a sulfhydryl-terminated oMMA which was precipitate by diethyl ether. The precipitate was filtered and washed with diethyl ether, and dried in vacuum. A block copolymer of oMMA and PAAc (oMMA-b-PAAc) was obtained by polymerization of acrylic acid using the sulfhydryl-terminated oMMA as a chain transfer agent and AIBN as an initiator, in DMF at 60° C. for 18 hours. The resulting block copolymer was precipitated by diethyl ether. The precipitate was filtered, washed with diethyl ether and dried in vacuum. This reaction scheme is illustrated below (in this scheme, m and n represent repetition of the monomer unit of methyl methacrylate and acrylic acid, respectively, and are greater than 10):

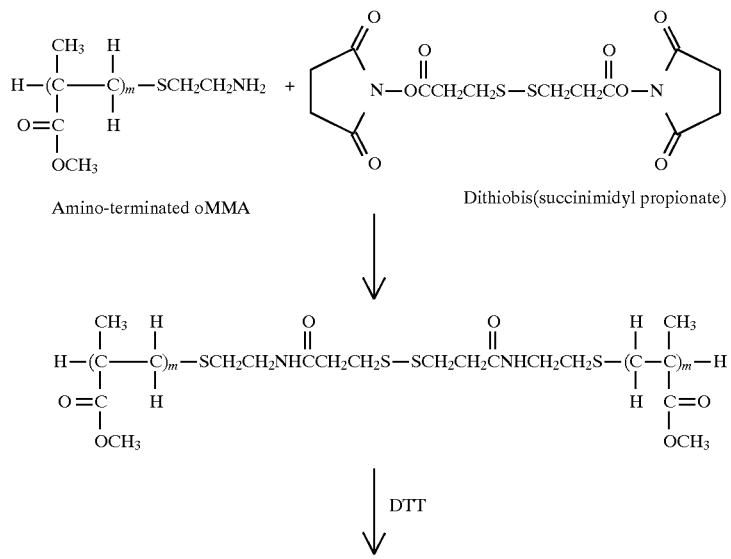

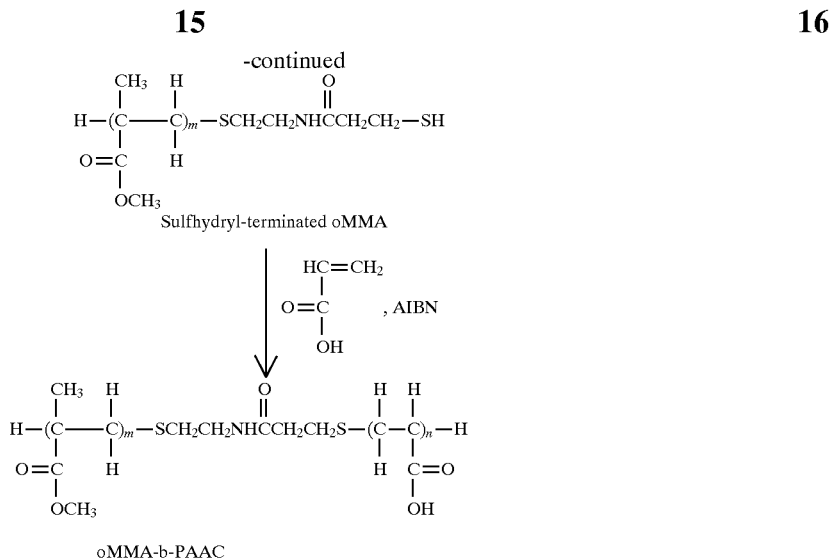

oMMA-b-PAAC

EXAMPLE 7

Agent Loading of Hydrophobically-Modified Bioadhesive Polyelectrolyte to Yield Polyelectrolyte-Agent Composition The block copolymer, oMMA-b-PAAc, of Example 6 was loaded with a representative agent, doxorubicin hydrochloride, by dissolving the same in DMF. The solution was then put into a dialysis tube having a molecular weight cut off ("MWCO") of 1000, and dialyzed against distilled water. Following dialysis, the content of the dialysis tube was recovered and centrifuged. The resulting supernatant was recovered, yielding the polyelectrolyte-agent composition in the form of a micelle.

The micelle was characterized by GPC, which was carried out using a Waters 501 type pump (Millipore Corp., Milford, Mass.) at a flow rate of 0.7 ml/min. at room temperature with Waters ultrahydrogel 250 and 500 columns with 50 nM PBS as the elluent. The column was calibrated by pulluran (Showa Dendo, Japan). The micelles were detected and confirmed by refraction index using a Waters 410 Differential Refractometer and by UV-VIS absorption (485 nm) using a Waters 486 UV detector.

EXAMPLE 8

Agent Release from Polyelectrolyte-Agent Composition

Agent release from the polyelectrolyte-agent composition (i.e., the micelle) of Example 7 was determined by placing the micelle-containing solution into a 1.5 ml polypropylene tube capped with a dialysis membrane (MWCO: 10,000). The tube was put into a 20 ml screw-capped glass vial filled with 10 ml PBS, and shaken by Orbit shaker at a shaking speed of 100 rpm. at room temperature. Next, 0.5 ml of the PBS solution was periodically withdrawn from the vial, and the amount of released agent determined spectrophotometrically. The volume of PBS solution within the vial was held constant by adding 0.5 ml of fresh PBS buffer after each sampling. The fractional release of drug was calculated as a function of time, with all data average over three determination. An aqueous solution of doxorubicin hydrochloride was used as a control.

Figure 6:
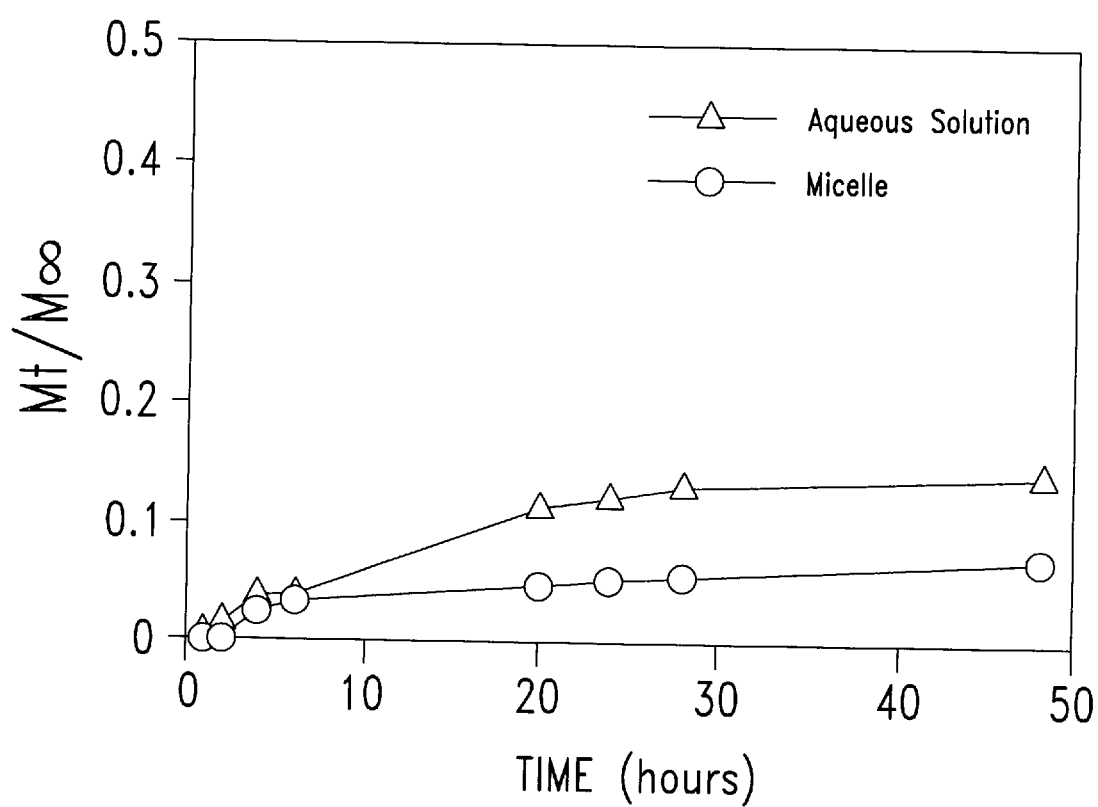
FIG. 6 illustrates release of doxorubicin hydrochloride from a block copolymer of PAAc and oMMA, oA-b-PAAc.

The results of this experiment are presented in FIG. 6. Referring to this figure, release of agent (i.e,. doxorubicin) from the polyelectrolyte-agent composition (i.e., the micelle) was relatively slow compared to the aqueous solution, which is beneficial for applications requiring a slow, sustained agent release of agent.

From the foregoing, it will be appreciated that, although specific embodiments of this invention have been described herein for the purposes of illustration, various modifications may be made without departing from the spirit and scope of the invention. Accordingly, the invention is not limited except by the appended claims.

We claim:

1. A hydrophobically-modified bioadhesive polyelectrolyte, comprising a non-crosslinked carboxylic acid-containing bioadhesive polyelectrolyte and a hydrophobic component covalently attached thereto:

wherein the carboxylic acid-containing bioadhesive polyelectrolyte is a polymer or copolymer comprising repeating units having a formula selected from:

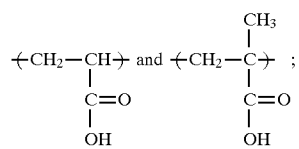

and the hydrophobic component is a polymer or copolymer comprising repeating units of the formula:

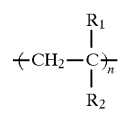

where n represents repeating monomers of the polymer or copolymer;

$R_1$ is selected from hydrogen and a saturated or unsaturated C1–C2 alkyl; and $R_2$ is selected from hydrogen, a saturated or unsaturated C1–C2 alkyl, a substituted or unsubstituted C6–C9 aryl, a substituted or unsubstituted C7–C11 arylalkyl, —C(=O)N($R_3$)($R_4$) and —C(=O)O$R_5$, where $R_3$ and $R_4$ are the same or different and independently selected from a saturated or unsaturated C1–C3 alkyl, and $R_5$ is selected from a saturated or unsaturated C1–C2 alkyl and —(CH$_2$)$_m$OH where m is $\geq$3.

2. The hydrophobically-modified bioadhesive polyelectrolyte of claim 1 wherein the hydrophobically-modified bioadhesive polyelectrolyte is a graft copolymer.

3. The hydrophobically-modified bioadhesive polyelectrolyte of claim 1 wherein the hydrophobically-modified bioadhesive polyelectrolyte is a block copolymer.

4. The hydrophobically-modified bioadhesive polyelectrolyte of claim 1 wherein the carboxylic acid-containing bioadhesive polyelectrolyte is polyacrylic acid.

5. The hydrophobically-modified bioadhesive polyelectrolyte of claim 1 wherein the carboxylic acid-containing bioadhesive polyelectrolyte is a homopolymer.

6. The hydrophobically-modified bioadhesive polyelectrolyte of claim 1 wherein the carboxylic acid-containing bioadhesive polyelectrolyte is a copolymer.

7. The hydrophobically-modified bioadhesive polyelectrolyte of claim 1 wherein the hydrophobic component is a homopolymer.

8. The hydrophobically-modified bioadhesive polyelectrolyte of claim 1 wherein the hydrophobic component is a copolymer.

9. The hydrophobically-modified bioadhesive polyelectrolyte of claim 1 wherein the hydrophobic component absorbs less than 10% by weight water.

10. The hydrophobically-modified bioadhesive polyelectrolyte of claim 1 wherein the hydrophobic component comprises at least two different hydrophobic polymers.

11. The hydrophobically-modified bioadhesive polyelectrolyte of claim 1 wherein the saturated or unsaturated alkyl is a saturated n-alkyl.

12. The hydrophobically-modified bioadhesive polyelectrolyte of claim 1 wherein the substituted or unsubstituted C6–C9 aryl is selected from phenyl, methylphenyl, dimethylphenyl and trimethylphenyl.

13. The hydrophobically-modified bioadhesive polyelectrolyte of claim 1 wherein the C7–C11 arylalkyl is selected from benzyl, methylbenzyl, dimethylbenzyl, phenylethyl and phenylpropyl.

14. The hydrophobically-modified bioadhesive polyelectrolyte of claim 1 wherein the hydrophobic polymer further comprises a hydrophilic monomer.

15. The hydrophobically-modified bioadhesive polyelectrolyte of claim 14 wherein the hydrophilic monomer is selected from 2-hydroxy ethyl methacrylate, vinyl pyrrolidone, vinyl acetate and acrylamide.

16. The hydrophobically-modified bioadhesive polyelectrolyte of claim 1 wherein the hydrophobic polymer is attached to the bioadhesive polyelectrolyte at a weight ratio ranging from 3% to 30%.

17. A polyelectrolyte-agent composition, comprising a hydrophobically-modified bioadhesive polyelectrolyte of any one of claims 1–3, 4–6, 7–10 and 11–16 in combination with an active agent.

18. The polyelectrolyte-agent composition of claim 17 wherein the composition is in the form of a particle or film, or the composition further comprises a solvent and is in the form of a solution or a dispersion of micelles.

19. The polyelectrolyte-agent composition of claim 17 wherein the agent is a hydrophobic agent.

20. The polyelectrolyte-agent composition of claim 17 wherein the agent has a hydrophobic portion and an ionic portion.

21. The polyelectrolyte-agent composition of claim 17 wherein the agent has multiple cationic charges.

22. The polyelectrolyte-agent composition of claim 17 wherein the agent is a drug.

23. The polyelectrolyte-agent composition of claim 17 wherein the agent is selected from a protein and a peptide.

24. The polyelectrolyte-agent composition of claim 17 formulated for topical or systemic administration.

25. The polyelectrolyte-agent composition of claim 17 formulated as a solution, cream, gel, ointment or powder.

* * * * *